(12) United States Patent
Juntunen et al.

(10) Patent No.: US 10,570,383 B2
(45) Date of Patent: Feb. 25, 2020

(54) VARIANTS OF FUNGAL CELLULASE

(71) Applicant: AB Enzymes Oy, Rajamäki (FI)

(72) Inventors: Kari Juntunen, Espoo (FI); Leena Valtakari, Rajamäki (FI); Susanna Mäkinen, Läyliäinen (FI); Marika Alapuranen, Tuusula (FI); Hendrik Hellmuth, Darmstadt (DE); Pentti Ojapalo, Tuusula (FI); Marc Mennicken, Köln (DE); Ulrich Schwaneberg, Kelmis-Hergenrath (BE); David Schönauer, Aachen (DE); Terhi Puranen, Hyvinkää (FI)

(73) Assignee: AB Enzymes Oy, Rajamäki (FI)

( * ) Notice: Subject to any disclaimer, the term of this patent is extended or adjusted under 35 U.S.C. 154(b) by 69 days.

(21) Appl. No.: 15/850,712

(22) Filed: Dec. 21, 2017

(65) Prior Publication Data

US 2019/0194634 A1    Jun. 27, 2019

(51) Int. Cl.
| | |
|---|---|
| *C12N 9/26* | (2006.01) |
| *C12N 15/00* | (2006.01) |
| *C12N 9/42* | (2006.01) |
| *C11D 3/386* | (2006.01) |
| *C11D 3/00* | (2006.01) |
| *C11D 11/00* | (2006.01) |
| *D06M 16/00* | (2006.01) |

(52) U.S. Cl.
CPC .......... *C12N 9/2437* (2013.01); *C11D 3/0036* (2013.01); *C11D 3/38645* (2013.01); *C11D 11/0017* (2013.01); *C12N 15/00* (2013.01); *D06M 16/003* (2013.01)

(58) Field of Classification Search
None
See application file for complete search history.

(56) References Cited

U.S. PATENT DOCUMENTS

| 7,741,093 B2 | 6/2010 | Vehmaanpera et al. |
| 2002/0168751 A1 | 11/2002 | Miettinen-Oinonen et al. |

FOREIGN PATENT DOCUMENTS

| EP | 1874927 B1 | 3/2014 |
| EP | 0857216 B1 | 9/2014 |
| WO | 9812307 A1 | 3/1998 |
| WO | 2006/117432 A1 | 11/2006 |
| WO | 2016066896 A1 | 5/2016 |
| WO | 2017/084560 A1 | 5/2017 |
| WO | 2017/106676 A1 | 6/2017 |

OTHER PUBLICATIONS

Gao et al. Characterization and crystal structure of a thermostable glycoside hydrolase family 45 1,4-?-endoglucanase from Thielavia terrestris. Enzyme and Microbial Technology, 17. Jan. 2017 (online). vol. 99, p. 32-37 & sequence alignment between TtCel45 sequence and Seq ID No. 1 residues 22-235 of the current application chapter 3. Results and discussion.

Valjakka et al. Structure of 20K endoglucanase from Melanocarpus albomyces at 1.8 Å resolution. Acta cystallographica. Section D, Biological crystallography, 2003. vol. 59, p. 765-768 whole document, especially Figure 1.

Sambrook, J. and Russell, D.W. (2001) Plasmids and Their Usefulness in Molecular Cloning, Molecular Cloning a Laboratory Manual (3rd ed.), pp. 1.31-1.42, 1.62-1.64, Cold Spring Harbor, NY: Cold Spring Harbor Laboratory Press.

Paloheimo, M. et al, High-Yield Production of a Bacterial Xylanase in the Filamentous Fungus Trichoderma reesei Requires a Carrier Polypeptide with an Intact Domain Structure, Applied and Environmental Microbiology, Dec. 2003, vol. 69, No. 12, pp. 7073-7082.

Penttila, M. et al, A Versatile Transformation System for the Cellulolytic Filamentous Fungus Trichoderma Reesei, Gene, 1987, vol. 61, pp. 155-164.

Joutsjoki, V.V. et al, Transformation of Trichoderma reesi with the Hormoconis resinae glucoamylase P (gamP) Gene: Production of a Heterologous Glycoamylase by Trichoderma reesi, Current Genetics, 1993, vol. 24, pp. 223-228.

Karhunen T. et al, High Frequency One-Step Gene Replacement in Trichoderma reesi. I. Endoglucanase I overproduction, Mol Gen Genet, 1993, vol. 241, pp. 515-522.

Haakana, H. et al, Cloning of Cellulase Genes from Melanocarpus albomyces and Their Efficient Expression in Trichoderma Reesi, Enzyme and Microbial Technology, 2004, vol. 34, pp. 159-167.

Henrissat, B., et. al., New Families in the Classification of Glycosyl Hydrolases Based on Amino Acid Sequences, Biochem. J., 1993, vol. 293, pp. 781-788.

Henrissat, B., A Classification of Glycosyl Hydrolases Based on Amino Acid Sequence Similarities, Biochem. J., 1991, vol. 280, pp. 309-316.

Henrissat, B. et al, Updating the Sequence-Based Classification of Glycosyl Hydrolases, Biochem. J., 1996, vol. 316, pp. 695-696.

Bailey, M.J. et al, Induction, Isolation and Testing of Stable Trichoderma reesi Mutants with Improved Production of Solubilizing Cellulase, Enzyme Microb. Technol., 1981, vol. 3, pp. 153-157.

Kadowaki, M. et al., Functional Characterization and Low-Resolution Structure of an Endoglucanase Cel45A from the Filamentous Fungus Neurospora crass OR74A: Thermostable Enzyme with High Activity Toward Lichenan and beta-Glucan, Mol. Biotechnol., 2015, vol. 57, pp. 574-588.

*Primary Examiner* — Yong D Pak
(74) *Attorney, Agent, or Firm* — Banner & Witcoff, Ltd.

(57) ABSTRACT

The present invention relates to polypeptides having cellulase activity, in particular to variants derived from the 20K-cellulase enzyme. The invention discloses a number of amino acid residue positions important for the properties of the cellulase enzyme and thereby for the stability and/or performance thereof. The novel variants have improved stability compared to the parental cellulase. In particular, the novel variants have good performance in an antigreying application and excellent stability in the presence of a protease in several detergent compositions even in long-term experiments.

17 Claims, 6 Drawing Sheets

Specification includes a Sequence Listing.

VARIANTS OF FUNGAL CELLULASE

FIELD OF THE INVENTION

The present invention relates to polypeptides having cellulase activity, in particular the invention relates to variants of cellulolytic enzymes that hydrolyze cellulose. The enzymes have been engineered to have improved stability compared to the parent cellulase. Provided herein are novel polypeptide variants and the uses thereof.

BACKGROUND OF THE INVENTION

Cellulases or cellulolytic enzymes are enzymes involved in hydrolysis of cellulose. In the textile industry, cellulases are used in denim finishing to create a fashionable stone washed appearance in denim cloths in a biostoning process, and they are also used, for instance, to clean fuzz and prevent formation of pills on the surface of cotton garments. In detergent industry cellulases are used to brighten colors and to prevent graying, pilling of garments and to improve cleaning. Cellulases are further used in food industry and animal feed manufacturing, and they have a great potential in biomass hydrolysis and in the pulp and paper industry, for instance, in deinking to release ink from fiber surfaces and in improving pulp drainage.

The 20K-cellulase deriving from *Melanocarpus albomyces* has been used extensively for years in the textile and detergent industry and it has been a subject of several patents (for example EP0857216B1 and EP1874927B1). This cellulase has been shown to have good performance especially in antigreying applications. The native 20K-cellulase molecule was cloned in the 1990's. Current increased demand on different washing systems for laundry has substantial consequences for the composition and amount of detergents needed.

Although cellulolytic enzymes have been used successfully in commercial applications for many years, a need still exists for new cellulases with altered properties, such as improved stability in detergent formulations containing protease.

BRIEF DESCRIPTION OF THE INVENTION

An object of the present invention is to provide novel variants of the 20K-cellulase that show improved performance and stability in detergent, when compared to the parental enzyme. The objects of the invention are achieved by a variant polypeptides and a method for their preparation and its uses which are characterized by what is stated in the independent claims. The preferred embodiments of the invention are disclosed in the dependent claims.

The invention discloses a number of amino acid residue positions important for the stability of the 20K-cellulase enzyme and thereby for the performance thereof. The present invention provides variant cellulase polypeptides basing on *Melanocarpus albomyces* 20K-cellulase core (without CBD). The novel variants have improved stability compared to the parent cellulase MA0, deriving from the 20K-cellulase. In particular, the novel variants have good performance in an antigreying application and excellent stability in the presence of a protease in several detergent compositions. Especially the variants show improved stability in protease containing detergents even in long-term experiments at elevated temperatures like 30° C. and 37° C. In addition the yield of the variants in fermentation is comparable to parental cellulase MA0.

BRIEF DESCRIPTION OF THE DRAWINGS

In the following the invention will be described in greater detail by means of preferred embodiments with reference to the attached drawings, in which FIG. 1 schematically shows the expression plasmid constructions for the expression of the MA0 variants in *Trichoderma reesei*. Position of used promoter (Pcbh1), terminator (Tcbh1) and selection marker gene (amdS), relevant restriction sites and the position of the ampicillin resistance encoding gene (AmpR) in the vector are shown. Picture was generated using Geneious version 10.0 created by Biomatters.

DETAILED DESCRIPTION OF THE INVENTION

Cellulolytic enzymes or cellulases are enzymes having cellulolytic activity, which means that they are capable of hydrolysing cellulosic substrates or derivatives thereof into smaller saccharides. Cellulolytic enzymes thus include both cellulases and hemicellulases. Cellulases include (1) endoglucanases (EG, EC 3.2.1.4) which cut internal beta-1,4-glucosidic bonds; (2) exoglucanases or cellobiohydrolases (CBH, EC 3.2.1.176, EC 3.2.1.91) that cut the dissaccharide cellobiose from the reducing or non-reducing end of the cellulose polymer chain and (3) beta-1,4-glucosidases (BG, EC 3.2.1.21) which hydrolyze the cellobiose and other short cello-oligosaccharides to glucose.

The present invention relates in particular to endoglucanases. Specifically, the present invention relates to fungal endoglucanases belonging to glycosyl hydrolase family 45 (Cel45), especially to variants of these endoglucanases. More specifically, the invention relates to MA0 cellulase variants deriving of *Melanocarpus albomyces* ALK04237 20 kDa endoglucanase. "Glycosyl hydrolase family 45" or "GH45" refers to the glycosyl hydrolase family as defined by Henrissat 1991, and Henrissat and Bairoch 1993, 1996.

The design of mutants is based on MA0 cellulase 3D structure and sequence comparisons of Cel45 family enzymes. The amino acid and nucleotide sequences of *Melanocarpus albomyces* Cel45 20K-cellulase derived MA0 is set forth in SEQ ID NO: 1 and SEQ ID NO: 2, respectively. The isolation, enzymatic activity and industrial applications of 20K-cellulase are disclosed for example in EP1874927B1 and EP0857216B1 (AB Enzymes Oy).

The present invention specifically relates to a cellulase variant polypeptide, or an active fragment thereof, wherein the variant polypeptide has cellulase activity and comprises an amino acid sequence having at least 90%, but less than 100% sequence identity to residues 22-235 of SEQ ID NO:1 comprising at least one substitution or deletion at one or more position selected from: 2, 22, 33, 35, 39, 44, 48, 54, 75, 82, 92, 99, 108, 122, 174, 175, 177, 194, 205, 206, 207, 208, 209, 210, 211, 212, 213, and 214 wherein the amino acid positions of said variant polypeptide or active fragment thereof are numbered by correspondence with the mature amino acid sequence of SEQ ID NO:3.

The invention further relates to a polypeptide comprising one or more of the following substitutions or deletions in the cellulase amino acid sequence set forth in SEQ ID NO:1: N2W, N2R, G22A, G22S, G22V, A33R, F35W, F35M, H39P, H39S, V44R, V44Q V44W, V44L, E48D, S54M, S54A, S54T, S54L, S54V A75H, A75S, A75R, E82S, E82R, E82W, T92I, A99Q T108I, N122A, N122L, N122S, N122G, N122T, N122V, N122I, Q174R, N175D, D177Q, D177E, A194Q, G205T, F206H, A207R, A207S, del(A207-A214), del(V208-A214), del(F209-A214), del(K210-A214), del(A211-A214), del(P212-A214) and del(S213-A214) wherein the amino acid positions of said variant polypeptide are numbered by correspondence with the mature amino acid sequence of SEQ ID NO:3.

The invention further relates to a variant polypeptide, wherein the variant comprises a substitution at amino acid positions 22 and/or 122, wherein at position 22 G is substituted to A, S or V and at position 122 N is substituted to A, S, G, T, V or I. In one embodiment the variant comprises a substitution at positions 22 and 122. It may additionally comprise at least one further substitution and/or deletion. The further substitution may be at a position selected from the following positions: 2, 35, 44, 54, 75, 82, 108, 174, 177, 205, 206 and 207 and the deletion may be selected from the following: del(A207-A214), del(V208-A214), del(F209-A214), del(K210-A214), del(A211-A214), del(P212-A214) or del(S213-A214).

In the present invention the variants are derived from a parental molecule MA0 (SEQ ID NO: 2), which is a polynucleotide encoding for the catalytic core domain of a cellulase derived from *Melanocarpus albomyces* ALK04237 20K-cellulase having no cellulose binding domain (CBD).

The term "variant" as used herein refers to a polypeptide having cellulase activity and comprising an experimentally induced mutation, i.e., a, insertion, substitution, and/or deletion, at one or more positions compared to the parental sequence MA0 set forth in SEQ ID NO:1. MA0 differs from 20K-cellulase amino acid sequence by having a mutation in one specific position. A substitution means a replacement of an amino acid occupying a position with a different amino acid; a deletion means removal of an amino acid occupying a position; and an insertion means the addition of one or more amino acids. Deletions are described herein using "del" before an indication of the first and last amino acid(s) deleted.

The polypeptide variant preferably comprises a sequence that is at least 90%, 91%, 92%, 93%, 94%, 95%, 96%, 97%, 98% or at least 99% but less than 100% identical to SEQ ID NO:1. In some embodiments, the disclosed variant sequence comprises at least one mutation and the remainder of the sequence is at least 90% identical to the amino acid residues 22-235 set forth in SEQ ID NO: 1. As used herein, "identity" means the percentage of exact matches of amino acid residues between two aligned sequences over the number of positions where there are residues present in both sequences. When one sequence has a residue with no corresponding residue in the other sequence, the alignment program allows a gap in the alignment, and that position is not counted in the denominator of the identity calculation. Identity is a value determined with the Pairwise Sequence Alignment tool EMBOSS Needle at the EMBL-EBI website (www.ebi.ac.uk/Tools/psa/emboss_needle/) with the following parameters: BLOSUM62, Gap open 10, Gap extend 0.5.

The variants are generated by deliberately introducing changes in DNA to produce mutant gene products i.e. proteins. The changes or modifications of the parental nucleotide sequence may be introduced by several methods including e.g. site-directed and random mutagenesis, recombination or recombinant fusion engineering. For site-directed mutagenesis and fusion engineering a protein structure and good understanding of the structure-function relationship is beneficial. In the absence of such deep understanding, methods based on random mutagenesis may be used.

A variant may be obtained e.g. by altering hydrogen bond contacts, altering charge distribution, introduction of a salt bridge, introduction of metal binding sites, filling an internal structural cavity with one or more amino acids with bulkier side groups (in e.g. regions which are structurally mobile), substitution of histidine residues with other amino acids, removal of a deamination site, removal of a flexible region, truncation of terminal region, shortening of a loop or by helix capping. Stability of the protein may be improved by substitution of at least one amino acid with cysteine residue or insertion of one or more cysteine residues which creates at least one disulfide bridge.

The cellulase polypeptide variants of the invention are preferably recombinantly produced non-naturally occurring proteins. They are conveniently prepared using the generally known recombinant DNA technology. Briefly, the polynucleotide encoding the endoglucanase is cloned and inserted into an expression vector, transformed into a host cell and expressed. Preferably, mutations are introduced into the coding sequence with codons preferred by the host strain used. Methods for protein production by recombinant technology in different host systems are well known in the art. Preferably, the polypeptide variants are produced as extracellular proteins that are secreted into the culture medium, from which they can easily be recovered and isolated.

The polypeptide variants may be designed to comprise in addition to the catalytic core domain, which forms the active or functional site of the enzyme, one or more "cellulose binding domains" ("CBDs"), also named as carbohydrate binding domains/modules (CBD/CBM) located either at the N- or C-terminus of the catalytic domain. CBMs have carbohydrate-binding activity and they mediate the binding of cellulase to crystalline and amorphous cellulose but have little or no effect on hydrolytic activity of the enzyme on soluble substrates.

The variants of the invention may optionally also contain a linker connecting the CBM and catalytic domain via a flexible and usually highly glycosylated region. By the term "linker" or "spacer" is meant a polypeptide comprising at least two amino acids which may be present between the domains of a multidomain protein, for example an enzyme comprising an enzyme core and a binding domain such as a carbohydrate binding module (CBM) or any other enzyme hybrid, or between two proteins or polypeptides produced as a fusion polypeptide, for example a fusion protein comprising two core enzymes. For example, the fusion protein of an enzyme core with a CBM is provided by fusing a DNA sequence encoding the enzyme core, a DNA sequence encoding the linker and a DNA sequence encoding the CBM sequentially into one open reading frame and expressing this construct. The modular structure of cellulases containing carbohydrate binding module and/or the linker region is well known in the art. The carbohydrate binding module and the linker region may be heterologous or homologous. "Heterologous" as used in the present context means that the CBM and/or the possible linker part of the variant polypeptides are obtained from a different organism than the cellulolytically active core domain. "Homologous" as used herein means that the CBM and/or the possible linker part of the variant are from the same organism as the cellulolytically active core. The invention discloses that any linker or CBM may be used in the variant polypeptide.

The variants of the invention may optionally also contain a signal sequence. The term "signal sequence" denotes a DNA sequence that encodes a polypeptide (a "secretory peptide") that, as a component of a larger polypeptide, directs the larger polypeptide through a secretory pathway of a host cell in which it is produced. The secretory signal sequence can be native or it can be replaced with secretory signal sequence or carrier sequence from another source. Depending on the host cell, the larger peptide may be cleaved to remove the secretory peptide during transit through the secretory pathway.

"Enzymatically active fragment" refers to the part of a specific amino acid sequence that is long enough to have the desired enzymatic activity. In other words a fragment may be e.g. only the mature part of the polypeptide or even a subsequence of the mature part. It may or may not contain a linker and CBM domain. The enzymatic activity refers herein to cellulolytic activity meaning catalytic ability of the polypeptide to hydrolyse cellulose or derivatives thereof.

The present invention relates further to novel polynucleotides which encode the cellulase variant polypeptide of the invention. The polynucleotide comprises a nucleotide sequence having SEQ ID NO: 2 or fragments thereof long enough to encode enzymatically active cellulase variants, or a sequence encoding a novel polypeptide variant as defined above, including complementary strands thereof. The polynucleotides of the invention are recombinant molecules containing genetically engineered non-naturally occurring sequences. "Polynucleotide" as used herein refers to both RNA and DNA, and it may be single stranded or double stranded. It may also be complementary DNA (cDNA). With cDNA is meant a DNA molecule synthesized from a messenger RNA template obtained from a eukaryotic or prokaryotic organism. Further, the polynucleotide may be degenerate as a result of the genetic code to any one of the sequences as defined above. This means that different codons may code for the same amino acid.

The present invention relates to a recombinant expression "vector" comprising a polynucleotide encoding the polypeptide variants as characterized above, operably linked to regulatory sequences, which are capable of directing the expression of a gene encoding said polypeptide variants in a suitable host. Said regulatory sequences may originate from the host organism or from another organism. The expression vector may further comprise marker genes for selection of the transformant strains or the selection marker may be introduced to the host in another vector construct by co-transformation.

Still the present invention relates to a production "host", which can be any organism capable of expressing the desired polypeptide. As used herein, "host cell" means any cell type that is susceptible to transformation, transfection, transduction, mating, crossing or the like with a nucleic acid construct or expression vector comprising a polynucleotide. The term "host cell" encompasses any progeny that is not identical due to mutations that occur during replication. Non-limiting examples of a host cell are fungal cells, filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus, Chrysosporium, Myceliophthora* and *Humicola*; more preferably from the group consisting of Families Hypocreacea, Nectriaceae, Clavicipitaceae, Microascaceae, and Genera *Trichoderma* (anamorph of Hypocrea), *Fusarium, Gibberella, Nectria, Stachybotrys, Claviceps, Metarhizium, Villosiclava, Ophiocordyceps, Cephalosporium*, and *Scedosporium*; more preferably from the group consisting of *Trichoderma reesei* (*Hypocrea jecorina*), *T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum*, and *Scedosporium apiospermum*, and *Aspergillus niger, Aspergillus awamori, Aspergillus oryzae, Chrysosporium lucknowense, Myceliophthora thermophila, Humicola insolens*, and *Humicola grisea*, most preferably *Trichoderma reesei*. Non-limiting examples of a host cell are yeasts (e.g. *Saccharomyces cerevisiae, Pichia pastoris, Yarrowia lipolytica*) and bacterial cells, preferably gram positive Bacilli (e.g. *Bacillus subtilis, B. licheniformis, B. megaterium, B. amyloliquefaciens, B. pumilus*), gram-negative bacteria (e.g. *Escherichia coli*) and actinomycetales (e.g. *Streptomyces* sp.).

In an embodiment the host cell is a fungal cell, preferably a filamentous fungal cell, such as *Trichoderma* or *Trichoderma reesei*. In an embodiment the host cell is a bacterial cell, preferably a gram positive *Bacillus* cell, such as *B. subtilis, B. licheniformis, B. megaterium, B. amyloliquefaciens* or *B. pumilus*.

A "recombinant cell" or "recombinant host cell" refers to a cell or host cell, which has been genetically modified or altered to comprise a nucleic acid sequence which is not native to said cell or host cell. In an embodiment the genetic modification comprises integrating the polynucleotide in the genome of the host cell. In another embodiment the polynucleotide is exogenous in the host cell.

The present invention relates also to a method for producing variant polypeptides of the invention, said method comprising the steps of transforming a host cell with an expression vector encoding said polypeptide, and culturing said host cell under conditions enabling production of said polypeptide, and optionally recovering and purifying said polypeptide. The production medium may be a medium suitable for growing the host organism and optionally containing inducers for efficient gene expression.

The present invention relates to an enzyme composition comprising the variant cellulase polypeptides of the invention. As used in the present context the "enzyme composition" refers to any enzyme product, preparation or composition, which comprises at least one of the novel variant cellulase polypeptides described herein. Such an enzyme composition may be a spent culture medium or filtrate containing one or more variant cellulase polypeptides, or one or more variant cellulase polypeptides and one or more other enzymes. Spent culture medium means the culture medium of the host comprising the produced enzymes. Preferably the host cells are separated from said medium after the production. The enzyme composition may be a "whole culture broth" optionally after inactivating the production host(s) or microorganism(s) without any biomass separation, down-stream processing or purification of the desired cellulolytic enzyme(s), because the variant polypeptides can be secreted into the culture medium, and they display activity in the ambient conditions of the spent culture medium.

The enzyme composition may contain the enzymes in at least partially purified and isolated form. It may even essentially consist of the desired enzyme or enzymes. If desired, the enzyme compositions may be dried, spray-dried or lyophilized, granulated or the enzymatic activity may be otherwise concentrated and/or stabilized for storage. If required, a desired enzyme may be crystallized or isolated or purified in accordance with conventional methods, such as filtration, extraction, precipitation, chromatography, affinity chromatography, electrophoresis, or the like.

In one embodiment of the present invention the enzyme composition further comprises one or more additional enzymes selected from the group consisting of protease, lipase, cutinase, amylase, carbohydrase, cellulase, pectinase, pectatelyase, pectinolytic enzyme, esterase, phytase, mannanase, arabinase, galactanase, xylanase, oxidase, xanthanase, xyloglucanase, DNAse, laccase, and/or peroxidase, preferably selected from the group consisting of proteases, amylases, cellulases and lipases.

The present enzyme composition comprising cellulase and an additional enzyme is advantageous in providing synergistic effects. Such additional enzymes are desired when the present enzyme composition comprising cellulase is used in detergents e.g. when washing stains. Particularly advantageous synergistic enzymes that work with cellulases are amylases, proteases and mannanases, or a combination thereof, such as a composition comprising cellulase, amylase and protease. The perfect combination of enzymes allows maximal performance.

In general the properties of the selected enzyme(s) should be compatible with the selected detergent, (i.e., pH-optimum, compatibility with other enzymatic and non-enzymatic ingredients, etc.), and the enzyme(s) should be present in effective amounts. In an embodiment the present enzyme composition further comprises:
 a. at least one preservative selected from organic acids, e.g. benzoic acid, citric acid, ascorbic acid, sorbic acid, and salts thereof, sodium benzoate, hydroxybenzoate, benzisothiazolinone (BIT) or a combination thereof;
 b. optionally at least one polyol selected from propylene glycol, glycerol, a sugar, sugar alcohol, sorbitol, hexylene glycol
 c. optionally at least one inhibitor selected from formic acid, lactic acid, boric acid, boric acid derivative, aromatic borate ester, phenyl boronic acid derivative, peptide, other reversible subtilisin inhibitors or a combination thereof;
 d. optionally at least one enzyme selected from proteases, amylases, cellulases, lipases, xylanases, mannanases, cutinases, esterases, phytases, DNAses, pectinases, pectinolytic enzymes, pectate lyases, carbohydrases, arabinases, galactanases, xanthanases, xyloglucanase, laccases, peroxidases and oxidases with or without a mediator, or a combination thereof;
 e. optionally at least one salt selected from sodium chloride, potassium chloride, potassium (hydrogen)phosphate, sodium (hydrogen)phosphate, ammonium sulfate, potassium sulfate, or a combination thereof; and
 f. optionally at least one filler or carrier selected from maltodextrin, flour, sodium chloride, sulfate, sodium sulfate, sodium acid pyrophosphate, tetrasodium pyrophosphate, polyethylene glycol, or a combination thereof.

The additional components a-f provide improved properties for the present enzyme composition. The enzyme composition is compatible with the additional components and improves applicability of the enzyme composition in various uses. Salts, such as sodium chloride and sodium sulfate function as drying aids.

In an embodiment the present enzyme composition is in the form of a liquid composition or a solid composition such as solution, dispersion, paste, powder, granule, granulate, coated granulate, tablet, cake, crystal, crystal slurry, gel or pellet.

The enzyme composition can be used in cleaning agents or boosters that are added on top of the detergent during or before the wash and that are for example in the form of liquid, gel, powder, granules or tablets. The enzyme composition and detergent components may also be soaked in a carrier like textiles.

In an embodiment the enzyme composition is used in textile and detergent industry, biomass processing and biomass hydrolysis, preferably in biofuel, starch, pulp and paper, food, baking, feed or beverage industries.

The present invention relates further to a detergent composition comprising at least one of the novel variant cellulase polypeptides or an enzyme composition thereof. The invention relates also to a use of the variant cellulase polypeptides of the invention in detergent applications. The terms "detergent composition" and "detergent" include, unless otherwise indicated, all washing agents in any form such as solid, granular or powder-form, liquid, gel or paste-form, and any combination thereof. The detergent composition may be in the form of a sachet, pouch, tablet or bar, including multi-compartment products. The detergent composition can be a free-flowing powder or a liquid. The terms include, unless otherwise stated, all-purpose or heavy-duty washing agents, especially cleaning detergents; liquid fine-fabric, specialty or low-duty detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners;

metal cleaners; as well as cleaning auxiliaries such as bleach additives and "stain-stick" or pre-treat types, and laundry aids.

The terms "detergent", "detergent composition" and "detergent formulation" are used in reference to mixtures, which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the cellulase variants according to the invention, the term encompasses detergents that may contain e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, buffers, preservatives, sod suppressors, solvents, and structurants for liquid detergents, structure elasticizing agents, enzyme inhibitors or stabilizers, enzyme activators, transferase(s), hydrolytic enzymes, oxido reductases, bluing agents and fluorescent dyes, antioxidants, and solubilizers.

A composition for use in solid laundry detergent, for example, may include 0.000001%-5%, such as 0.000005-2%, such as 0.00001%-1%, such as 0.00001%-0.1% of variant cellulase polypeptide by weight of the composition.

A composition for use in laundry liquid, for example, may include 0.000001%-3%, such as 0.000005%-1%, such as 0.00001%-0.1% of variant cellulase polypeptide by weight of the composition.

A composition for use in automatic dishwash, for example, may include 0.000001%-5%, such as 0.000005%-2%, such as 0.00001%-1%, such as 0.00001%-0.1% of variant cellulase polypeptide by weight of the composition.

The detergent composition may be in the form of a bar, a homogenous tablet, a tablet having two or more layers, a pouch having one or more compartments, a regular or compact powder, a granule, a paste, a gel, or a regular, compact or concentrated liquid. In one embodiment the detergent composition can be a laundry detergent composition, preferably a liquid or solid laundry detergent composition. There are a number of detergent formulation forms such as layers (same or different phases), pouches, as well as forms for machine dosing unit.

The variant cellulase polypeptides of the invention and enzyme compositions or detergent compositions containing them when used in detergent and textile industries have excellent performance and stability.

The term "stability" includes storage stability and stability during use, e.g. during a wash process (in wash stability). The stability of the cellulase according to the invention is described as a function of time, e.g. how much activity is retained when the cellulase is kept in solution, in particular in a detergent solution. The stability is influenced by many factors, e.g. pH, temperature, detergent composition e.g. proteases, stabilizers, builders, surfactants etc.

In the present invention the term "improved detergent stability" means that the cellulase variant retains its activity and/or performance in detergent solution, during storage and/or washing better than the parental enzyme. The stability may be assayed by determining the residual activity of the enzyme added to detergent after incubation at certain conditions for e.g. after 1 or several weeks incubation at 37° C. or lower temperatures or after shorter time at 50° C., like described in Examples 2, 4 and 5. The residual activity of cellulase may be determined using the method described in Example 1 or any other method disclosed in the literature. The stability may be measured also as wash performance after storage, e.g. as antigreying performance like described in Example 5.

The variant cellulase polypeptides and the enzyme compositions thereof may be used for treating any cellulosic material. In the present context, "cellulosic material" refers to any material comprising cellulose or derivatives thereof as a significant component. Such a material may be textile material, plants or material of plant origin used in food or animal feed, plant material for oil extraction, or wood-derived mechanical or chemical pulp or secondary fiber.

The term "textile" means any textile material including yarns, yarn intermediates, fibers, non-woven materials, natural materials, synthetic materials, and any other textile material, fabrics made of these materials and products made from fabrics (e.g., garments, linen and other articles). The textile or fabric may be in the form of knits, wovens, denims, non-wovens, felts, yarns, and towelling. The textile may be cellulose based, such as natural cellulosics including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

The cellulosic material is reacted with the variant polypeptides of the invention or the enzyme composition comprising said variant polypeptides under suitable conditions, such as appropriate pH, and temperature, and the reaction is allowed to continue for a time sufficient for the enzymatic reaction to take place, whereby at least partially hydrolyzed cellulosic material is obtained. The enzymes are added in an enzymatically effective amount either simultaneously e.g. in the form of an enzyme mixture, or sequentially.

The variant cellulase polypeptides and the enzyme compositions containing them may be added to detergent compositions to improve textile cleaning, for instance by removal of pigment dirt and byantiredeposition and antigreying. The variant cellulases may also improve fiber and color care properties by prevention and removal of fuzz and pills resulting in brightening or freshening of colors and softening. The terms "depilling" (removal of pilling) and "color revival" are typically used to describe the cellulase effects on old, used cotton textiles. The terms "antipilling" (prevention of pilling), "color maintenance" or "color care"

are typically used to describe cellulase effects on new garments. The effect of fiber and color care properties can be detected by visible and measurable decrease of lightness (i.e. increase of darkness) or change in color of colored cotton textiles exposed to repeated washing cycles. Standardized tests monitors of prepilled and unpilled, new fabrics are commercially available.

The variant endoglucanase polypeptides and the enzyme compositions containing them are especially useful in detergent applications as an anti-greying agent. As used herein, the term "antigreying performance" or "antigreying effects" mean antiredepositioning and pigment removal properties. With increasing number of wash cycles, pigments, particles and soluble soils, salts and other material can adhere on the textile fibers, most likely in areas with damaged cotton fibers. This can cause a greying effect and a darkening or yellowing of the cotton textile. By theory, cellulases hydrolyze the cellulose chains in these areas at random positions with amorphous structure, leading to the removal of fibers with attached particles or higher accessibility for surfactants, and therefore showing a whitening or anti-greying effect. In addition, traces of cellulosic material in the washing liquor may be digested, preventing the adhesion of such fibers at the cotton surface of the garment. These effects are called antigreying or antiredeposition and can be evaluated using optical measurements. Suitable test methods are generally known in the art and are typically based on using artificial ballast soil systems with standard white test fabrics in repeated washing cycles in washing machines. The antigreying effect can be tested also by a single wash as stressed test using redeposition liquid based on carbon black.

The variant cellulase polypeptides may also be added into detergent compositions to improve textile cleaning or stain removal by removal of pigmented dirt or by having synergistic effects on some stains with other enzymes typically used in detergents, like proteases, amylases, lipases, pectinases, and mannanases. Stain removal effect can be measured as increased lightness or change of color of stained material, e.g. in artificially soiled swatches or test cloths by optical measurements and is visually detectable as fading of stains.

The variant cellulase polypeptides and the enzyme compositions containing them may also be useful in finishing processes of the textile industry, such as biofinishing of fabrics, garments or yarn. As used in the present context, the expression "biofinishing" (also called depilling, defuzzing, dehairing or biopolishing) refers to the use of the variant enzymes in a controlled hydrolysis of cellulosic fibers in order to modify the fabric or yarn surface in a manner that permanently prevents the tendency for pilling, improves fabric handle like softness and smoothness, clears the surface structure by reducing fuzzing. Biofinishing results in clarification of colors, improves the drapability of the fabric and improves moisture absorbability, which may further improve also the dyeability. Biofinishing may be performed before, after or at the same time as dyeing.

Enzymatic depilling can be carried out at any stage during textile wet processing, preferably after optional desizing and/or bleaching, and similar conditions as in biostoning can be used. Textiles in garment form can be also treated.

The variant cellulase polypeptides and enzyme compositions containing them may be used in biostoning of denim. As used in the present context, the expression "biostoning" of fabric or garment means the use of enzymes in place of, or in addition to, pumice stones for the treatment of fabric or garment, especially denim to obtain an aged or worn look. The term "aged or worn look" means that as a result of uneven dye removal, there are contrasts between dyed areas and areas from which dye has been removed.

The liquor ratio (the ratio of the volume of liquid per weight of fabric) in both biostoning and biofinishing may range from about 3:1 to 20:1, preferably 5:1 to 10:1. The treatment time can vary between 15 min to 90 min and preferably between 30 min to 60 min. It should be emphasized that the enzyme dosage greatly depends on the type of the fabrics, machinery, process conditions (pH, temperature, liquor ratio, treatment time, denim load, process scale) and type of the enzyme preparation or composition. Typical process parameters for e.g. industrial biofinishing are pH 4.5-8 at temperature of 40-65° C. A person skilled in art is capable in defining suitable dosages and conditions.

Sequence Listing

SEQ ID NO:1 The full-length amino acid sequence of MA0 cellulase deriving from the *Melanocarpus albomyces* ALK04237 GH45 20K-cellulase including amino acids from Met1 to Ala235.

SEQ ID NO:2 The nucleotide sequence of the full-length MA0 cellulase deriving from *Melanocarpus albomyces* ALK04237 cel45 20K-cellulase.

SEQ ID NO:3 The amino acid sequence of the mature MA0 cellulase deriving from the *Melanocarpus albomyces* ALK04237 GH45 20K-cellulase including amino acids from Ala1 to Ala214.

Deposits

*Melanocarpus albomyces* ALKO4237 was deposited at the Centraalbureau Voor Schimmelcultures at Upsalalaan 8, 3584 CT, Utrecht, The Netherlands on 2 Mar. 2012 and assigned accession number CBS132099.

EXAMPLES

Standard molecular biology methods were used in the isolation and enzyme treatments of DNA (e.g. isolation of plasmid DNA, digestion of DNA to produce DNA fragments), in *E. coli* transformations, sequencing etc. The basic laboratory methods used were either as described by the enzyme, reagent or kit manufacturer or as described in the standard molecular biology handbooks, e.g. Sambrook and Russell (2001) or as described in the following examples.

Example 1

Production of *Melanocarpus albomyces* MA0 Variants in *Trichoderma reesei*

Figure 1:
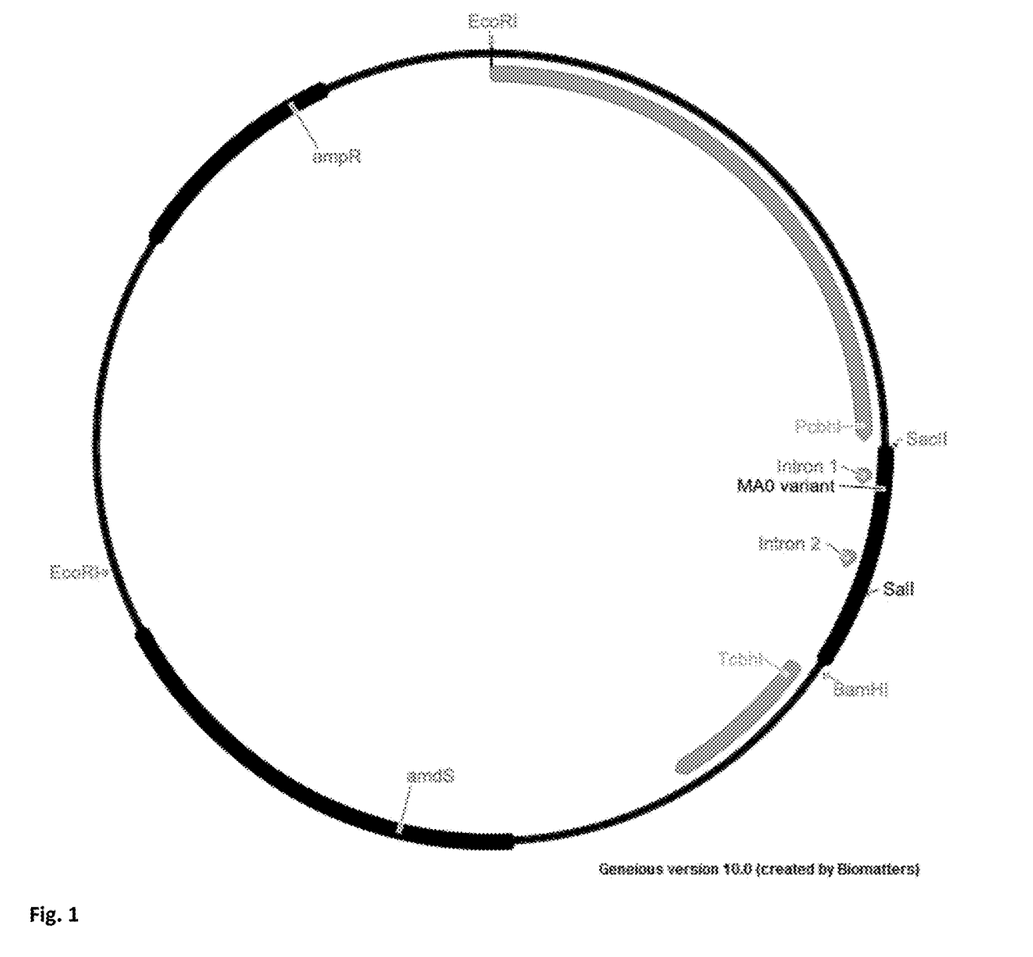

*Melanocarpus albomyces* cel45 20K-cellulase variants were derived from a parental molecule, designated here as MA0 (nucleic acid sequence SEQ ID NO: 2, corresponding to amino acid sequence SEQ ID NO: 1). Expression plasmids were constructed for production of recombinant cel45 MA0 variants (FIG. 1). The constructs contain *T. reesei* cel7 A promoter and terminator and the amdS marker gene as described in Paloheimo et al. 2003. The variant genes contain a signal sequence at position 1-63 nt and intron sequences at positions 84-154 nt and 404-473 nt. Synthetic genes, including mutations introduced in the core region of the parental molecule (Table 1), were exactly fused as SacII-BamHI fragments to the *T. reesei* cel7A promoter by ligation. For construction of the expression plasmid for MA79 variant a 328 bp SalI-BamHI fragment of pALK4472 was isolated and ligated into a 8523 bp SalI-BamHI fragment of pALK4458. Expression plasmids are listed in Table 1.

TABLE 1

The synthetic genes used in construction of the expression cassettes for production of MA0 cellulase variants in *T. reesei*. Amino acid positions are numbered by correspondence with the mature amino acid sequence without signal sequence (SEQ ID NO: 3).

| Gene/variant designation | Mutation | Expression plasmid |
|---|---|---|
| MA1 | G22A | pALK4458 |
| MA2 | P23R | pALK4459 |
| MA3 | F35W | pALK4460 |
| MA4 | F35D | pALK4461 |
| MA5 | H39S | pALK4462 |
| MA6 | H39P | pALK4463 |
| MA7 | A43S | pALK4464 |
| MA8 | V44R, E48D | pALK4465 |
| MA9 | V44Q | pALK4466 |
| MA10 | F53Y | pALK4467 |
| MA11 | A62S | pALK4468 |
| MA13 | E82S | pALK4470 |
| MA14 | A99Q | pALK4471 |
| MA15 | N122A | pALK4472 |
| MA16 | N122L | pALK4473 |
| MA17 | L130G | pALK4474 |
| MA18 | P136S | pALK4475 |
| MA19 | S151D | pALK4476 |
| MA20 | Q153S | pALK4477 |
| MA21 | D156S | pALK4478 |
| MA22 | P161S | pALK4479 |
| MA24 | V193T | pALK4481 |
| MA25 | V193D | pALK4482 |
| MA26 | A194Q | pALK4483 |
| MA27 | F206Y | pALK4484 |
| MA28 | S54M, N122A | pALK4485 |
| MA29 | G22A, E82S | pALK4486 |
| MA30 | F35W, H39P | pALK4487 |
| MA31 | H39S, V44Q | pALK4488 |
| MA32 | A43S, F53Y | pALK4489 |
| MA35 | F53T, P136S | pALK4492 |
| MA37 | V44R, E48D, G22A, E82S | pALK4494 |
| MA40 | A19D | pALK4497 |
| MA41 | K21E | pALK4498 |
| MA42 | K21Q | pALK4499 |
| MA43 | G20R | pALK4209 |
| MA44 | S30L | pALK4210 |
| MA45 | S30P | pALK4211 |
| MA46 | A33R | pALK4212 |
| MA47 | F35M | pALK4213 |
| MA48 | Q36R | pALK4214 |
| MA49 | V44L | pALK4215 |
| MA50 | E48I | pALK4216 |
| MA52 | A75S | pALK4218 |
| MA53 | A75H | pALK4219 |
| MA54 | T92I | pALK4220 |
| MA55 | T94R | pALK4221 |
| MA56 | T108I | pALK4222 |
| MA57 | F131I | pALK4223 |
| MA59 | Q174H | pALK4225 |
| MA60 | N175D | pALK4226 |
| MA61 | D177Q | pALK4227 |
| MA62 | V193I | pALK4228 |
| MA63 | A194S | pALK4229 |
| MA64 | G205R | pALK4230 |
| MA65 | A207R | pALK4231 |
| MA66 | A207S | pALK4232 |
| MA67 | A33L | pALK4233 |
| MA68 | Q36H | pALK4234 |
| MA69 | V44L, E48I | pALK4235 |
| MA70 | A33L, F35M, Q36R | pALK4236 |
| MA71 | N175D, D177Q | pALK4237 |
| MA72 | T92I, T94R | pALK4238 |
| MA73 | G205R, A207S | pALK4239 |
| MA74 | P124C, G165C | pALK4240 |
| MA75 | S5C, F119C, V105I | pALK4241 |
| MA76 | F35C, A56C | pALK4242 |
| MA77 | S68C, M103C, V105I | pALK4243 |
| MA78 | V186C, A207C | pALK4244 |
| MA79 | G22A, N122A | pALK4621 |
| MA80 | N122S | pALK4718 |
| MA81 | N122G | pALK4719 |
| MA82 | N122T | pALK4720 |
| MA83 | N122V | pALK4721 |
| MA84 | N122I | pALK4722 |
| MA85 | G22S | pALK4723 |
| MA86 | G22V | pALK4724 |
| MA87 | G22A, S54A, N122A | pALK4725 |
| MA88 | G22A, S54T, N122A | pALK4726 |
| MA89 | G22A, S54L, N122A | pALK4727 |
| MA90 | G22A, S54V, N122A | pALK4728 |
| MA91 | G22A, E82R, N122A | pALK4729 |
| MA92 | G22A, E82W, N122A | pALK4730 |
| MA93 | G22A, T108I, N122A | pALK4731 |
| MA94 | G22A, V44R, N122A | pALK4732 |
| MA95 | G22A, V44W, N122A | pALK4733 |
| MA96 | G22A, V44L, N122A | pALK4734 |
| MA97 | G22A, A75S, N122A | pALK4735 |
| MA98 | G22A, A75R, N122A | pALK4736 |
| MA99 | G22A, F35M, N122A | pALK4737 |
| MA100 | N2W, G22A, N122A | pALK4738 |
| MA101 | N2R, G22A, N122A | pALK4739 |
| MA102 | G22A, N122A, Q174R | pALK4740 |
| MA103 | G22A, N122A, G205T | pALK4741 |
| MA104 | G22A, F35W, A75H, T108I, N122A, A207S | pALK4742 |
| MA107 | G22A, N122A, Q174R, D177E | pALK4745 |
| MA109 | G22A, N122A, F206H | pALK4748 |
| MA110 | G22A, N122A, del(A207-A214) | pALK4749 |
| MA111 | G22A, N122A, del(V208-A214) | pALK4750 |
| MA112 | G22A, N122A, del(F209-A214) | pALK4751 |
| MA113 | G22A, N122A, del(K210-A214) | pALK4752 |
| MA114 | G22A, N122A, del(A211-A214) | pALK4753 |
| MA115 | G22A, N122A, del(P212-A214) | pALK4754 |
| MA116 | G22A, N122A, del(S213-A214) | pALK4755 |

The linear expression cassette was isolated from the vector backbone by EcoRI digestion or the circular plasmid was used directly in *T. reesei* protoplast transformation. The transformants were selected with acetamide as the sole nitrogen source. The host strain lacks the four major endogenous cellulases: CBHI/Cel7A, CBHII/Cel6A, EGI/Cel7B and EGII/Cel5A. The transformations were performed according to Penttilä et al, 1987, with the modifications described in Karhunen et al., 1993. The transformants were purified on selection plates through single conidia prior to sporulating them on potato dextrose agar.

The cellulase production of the transformants was analyzed from the culture supernatants of shake flask cultivations (50 ml). The transformants were grown for 7 days at 30° C., 250 rpm in a complex cellulase-inducing medium (Joutsjoki et al., 1993) buffered with 5% $KH_2PO_4$ at pH 5.5. The enzyme activity of the recombinant protein was measured from the culture supernatant as the release of reducing sugars from carboxymethylcellulose (3% CMC) at 50° C. in 50 mM HEPES buffer pH 7.0 essentially as described by Bailey and Nevalainen, 1981; Haakana, et al, 2004 (NCU activity). Production of the recombinant protein was also detected from the culture supernatant by sodium dodecyl sulfate polyacrylamide gel electrophoresis (SDS-PAGE).

Chosen transformants and the reference strain producing the parental MA0 cellulase were cultivated in shake flasks or bioreactors in complex cellulase-inducing medium to obtain material for the application tests (Examples 2 to 6).

Example 2

Screening of MA0 Variants MA1-MA79 Based on their Stability in Commercial Liquid Detergent at 50° C.

MA0 variants produced in *Trichoderma* as described in Example 1 were screened based on detergent stability at 50° C. by a rapid test in the presence of protease. Parental cellulase MA0 was used as reference. A 0.8% w/w amount of protease, Savinase 16L (Novozymes, Denmark), was added to a commercial liquid detergent containing no enzymes. The composition of detergent is described in Table 2. Culture supernatants of cellulases at 5% w/w were added to the detergent, and samples in plastic tubes with caps were incubated in a water bath at 50° C. for 30 minutes. The enzyme activity (NCU) was measured after incubation by the activity assay described in Example 1, except using longer reaction time of 30 minutes. Results were calculated as residual activity (%), which was obtained by dividing the activity of a sample after incubation at 50° C. by the initial activity of the sample.

TABLE 2

Composition of commercial liquid detergent

| Ingredient | % |
| --- | --- |
| Anionic surfactants | 15-30 |
| Nonionic surfactants, soap | 5-15 |
| Phosphonate, Soap | <5 |
| Boric acid | ≤1 |
| Other ingredients: e.g. optical brighteners, perfumes, preservatives | |
| pH 8.2-8.6 | |

Figure 2:
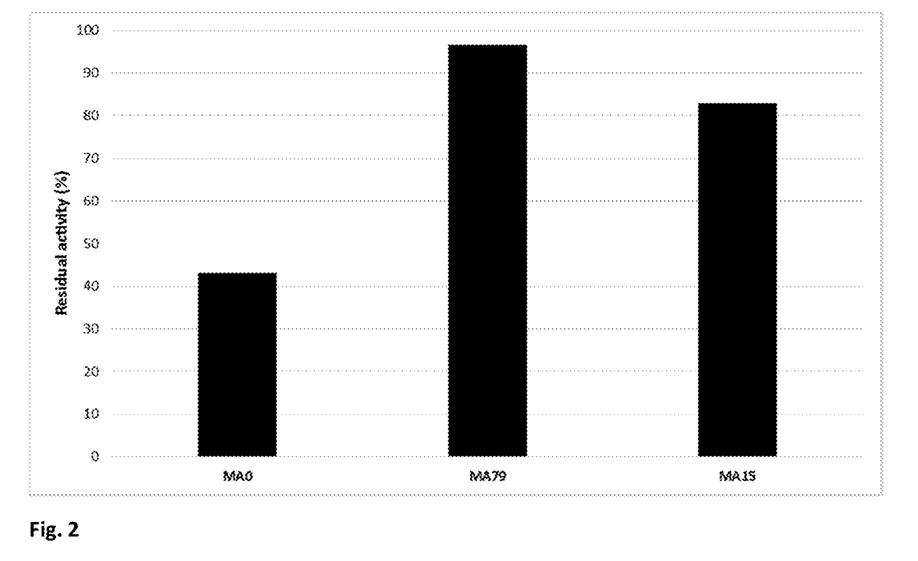
FIG. 2 shows the stability of variants MA79 and MA15 compared to parental cellulase MA0 as residual activity in commercial liquid detergent after incubating samples at 50° C. for 30 minutes in the presence of protease.

Several variants showed improved stability of enzyme activity in commercial liquid detergent at 50° C. compared to the parental MA0 cellulase. Results are shown in Table 3. Best stability was obtained with variants MA15, MA28 and especially MA79. Stability of variants MA15 and MA79 compared to MA0 is shown in FIG. 2 as residual activity. Both variants showed remarkably better stability than the parental cellulase.

TABLE 3

Stability of MA0 variants in detergent in the presence of protease (50° C., 30 min). Symbol "+" indicates improved stability (measured as residual activity) compared to parental MA0 cellulase, "+++++" indicates the best stability achieved in the test set.

| Variant | Stability |
| --- | --- |
| MA1 | ++ |
| MA3 | ++ |
| MA9 | ++ |
| MA14 | + |
| MA15 | ++++ |
| MA16 | +++ |
| MA26 | + |
| MA28 | ++++ |
| MA29 | +++ |
| MA30 | + |
| MA31 | + |
| MA37 | ++ |
| MA46 | + |

TABLE 3-continued

Stability of MA0 variants in detergent in the presence of protease (50° C., 30 min). Symbol "+" indicates improved stability (measured as residual activity) compared to parental MA0 cellulase, "+++++" indicates the best stability achieved in the test set.

| Variant | Stability |
| --- | --- |
| MA53 | + |
| MA54 | + |
| MA56 | + |
| MA61 | ++ |
| MA66 | +++ |
| MA71 | ++ |
| MA79 | +++++ |

Example 3

Testing the Antigreying Performance of MA0 Variants in Launder-Ometer

The most stable variant MA79 from Example 2 was tested for antigreying performance by a single wash method (40° C., 60 min, 16° dH) using carbon black (approx. 0.15 g/l) in a wash solution in addition to detergent (4.4 g/l). Parental cellulase MA0 was used as reference.

Cotton interlock double jersey with optical brighteners (CN-42) supplied from CFT (Center for Testmaterials NV, the Netherlands) was used as test fabric. The fabric was first prewashed in a washing machine (15 min 50° C. and 60 min at 60° C.) and tumble dried, then cutted to swatches of approx. 14-14.5 cm (total weight of 4 swatches 25 g).

As a source of carbon black RD-liq 01 from CFT containing 7 g of carbon black liquid (about 33% carbon black) in plastic bottles, that are normally intended for full scale washes in washing machine (one bottle per one single wash with test fabrics), were used. In this Example the method was adapted to small scale using approximately similar ratio of carbon black and water that would be in full scale. First a stock solution carbon black was prepared by placing an opened bottle of RD-liq 01 (i.e. about 2.3 g carbon black) in a decanter flask containing 1 liter of deionized water. The solution was stirred with a magnetic stirrer for overnight until the contents of the bottle were totally released. After that 65 g of stock solution mixed with 935 ml of synthetic tap water with hardness of 17.1° dH ending up to diluted carbon black solution having hardness of 16° dH and carbon black content approximately 0.15 g/l (or 0.45 g RD-liq 01).

For synthetic tap water with hardness of 17.1° dH the following stock solutions were prepared in deionized water (Milli-Q or equivalent):

Stock solution with 1000° d Calcium-hardness: $CaCl_2 \times 2 H_2O$ (1.02382.1000, Merck KGaA, Germany) 26.22 g/l Stock solution with 200° d Magnesium-hardness: $MgSO_4 \times 7 H_2O$ (1.05886.1000, Merck KGaA, Germany) 8.79 g/l $H_2O$ $NaHCO_3$ stock solution: $NaHCO_3$ (1.06329.1000 Merck KGaA, Germany) 29.6 g/l.

14.2 ml $CaCl_2$) solution, 14.2 ml $MgSO_4$ solution and 10.0 ml of freshly made $NaHCO_3$ solution were added in volumetric flask in the given order, made up to 1 liter with deionized water and mixed. The hardness of water was determined by complexometric titration and found correct.

Antigreying tests were performed in Atlas LP-2 Launder-Ometer as follows. Launder-Ometer was first preheated to 40° C. 60 g of steel balls (diameter 0.6 cm), 1.1 g of commercial liquid detergent described in Example 2, 250 ml of diluted carbon black liquor and diluted enzyme (<1.0 ml) were added into 1.2 liter containers. After that, 4 swatches of prewashed test fabric CN-42 were added and the Launder-Ometer was run at 40° C. for 60 min with a rotation speed of 42 rpm. Enzymes were dosed 0, 0.25, 0.05, 0.1 and 0.2 activity units (NCU) per liter. Activity was measured as described in Example 1.

After the cellulase treatment in Launder-Ometer, the swatches were first quickly rinsed separately under running tap water (ca. 20° C.) to remove the steel balls, then rinsed separately under running water in specific cups containing holes for 3 times and finally dipped in a bucket containing water. After that the swatches were extracted in a washing machine and let to dry on a grid at room temperature. Enzyme treated fabrics and controls without enzyme were rinsed and extracted separately to avoid contamination.

Antigreying performance of cellulase was evaluated by measuring reflectance of test fabrics by Konica Minolta CM3610A spectrophotometer as Y-value (illuminant D65/ 10°, 420 nm cut). Cellulase performance was calculated as $\Delta Y$ (delta Y), which means value Y of enzyme treated fabric minus value Y of fabric treated with carbon black and detergent containing washing liquor without enzyme (enzyme blank, control). Values were the average of 4 swatches. The higher the Y or $\Delta Y$ value, the better the antigreying effect and whiteness of the fabric.

Figure 3:
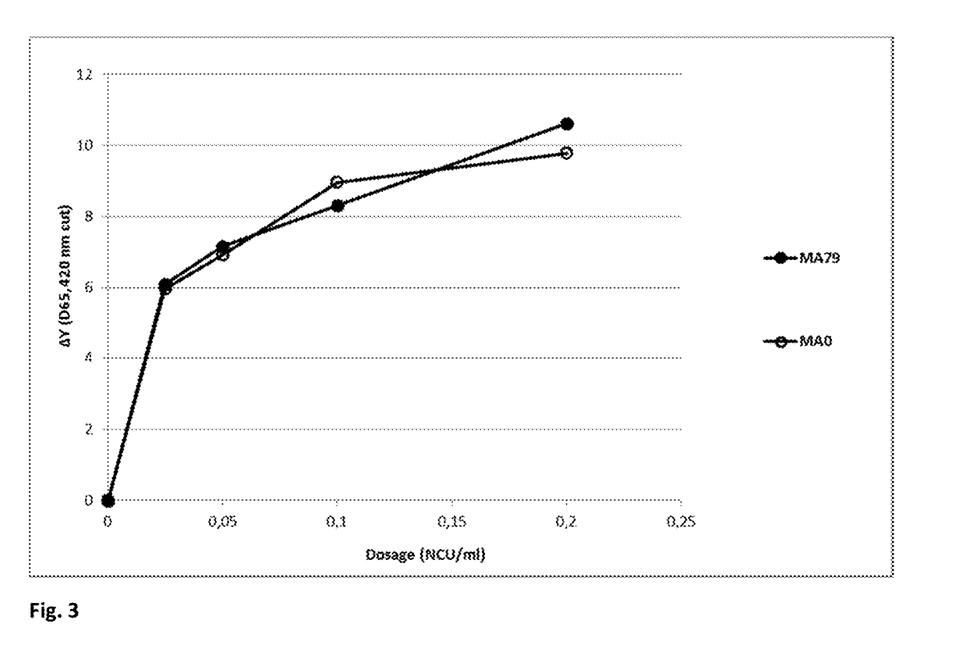
FIG. 3 shows the antigreying performance of variant MA79 and parental cellulase MA0 in a single wash in the presence of carbon black in a commercial liquid detergent. Washing conditions: 40° C., 60 min, 16° dH, carbon black approx. 0.15 g/l, detergent 4.4 g/l.

Results in FIG. 3 show that the most stable variant MA79 had excellent antigreying properties similar to parental MA0 cellulase in liquid detergent. Also several other variants from Example 2, like MA1, MA3, MA15, MA29, had as good antigreying performance as MA0 (data not shown).

Example 4

Long Term Stability of Variant MA79 in Liquid Detergent Measured as Enzyme Activity A cultivation sample of variant MA79 was tested for long term stability in a liquid detergent at 37° C., 30° C. and room temperature (approx. 20-22° C.), using parental cellulase MA0 as a reference. Tests were carried out with commercial liquid detergent described in Example 2 in the presence of added protease (0.8% w/w Savinase 16L). Cellulase preparations at 1% w/w were added to the detergent and samples in plastic tubes with caps were incubated at each temperature for several weeks or months. The enzyme activity was measured and results were calculated as residual activity as described in Example 2.

Figure 4A:
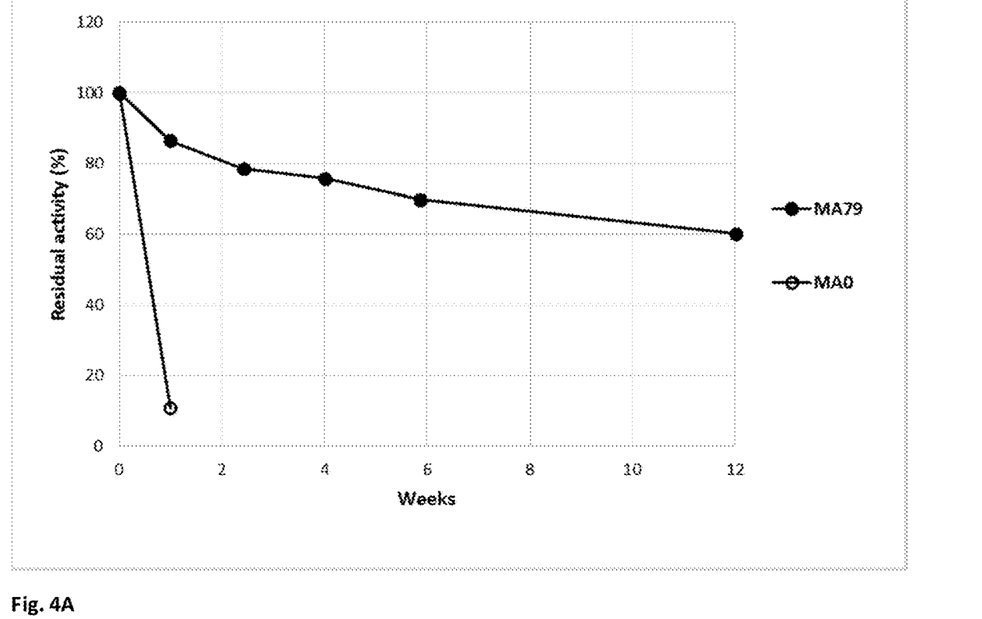
FIG. 4A shows the stability of variant MA79 compared to parental cellulase MA0 as residual activity in commercial liquid detergent at 37° C. in the presence of protease.
Figure 4B:
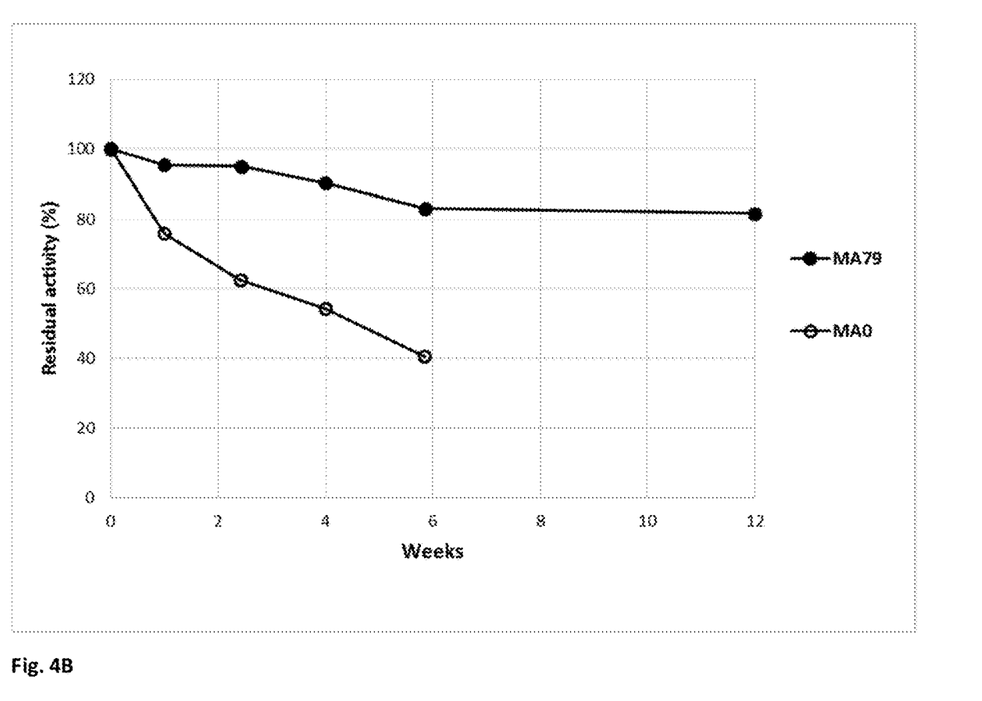
FIG. 4B shows the stability of variant MA79 compared to parental cellulase MA0 as residual activity in commercial liquid detergent at 30° C. in the presence of protease.
Figure 4C:
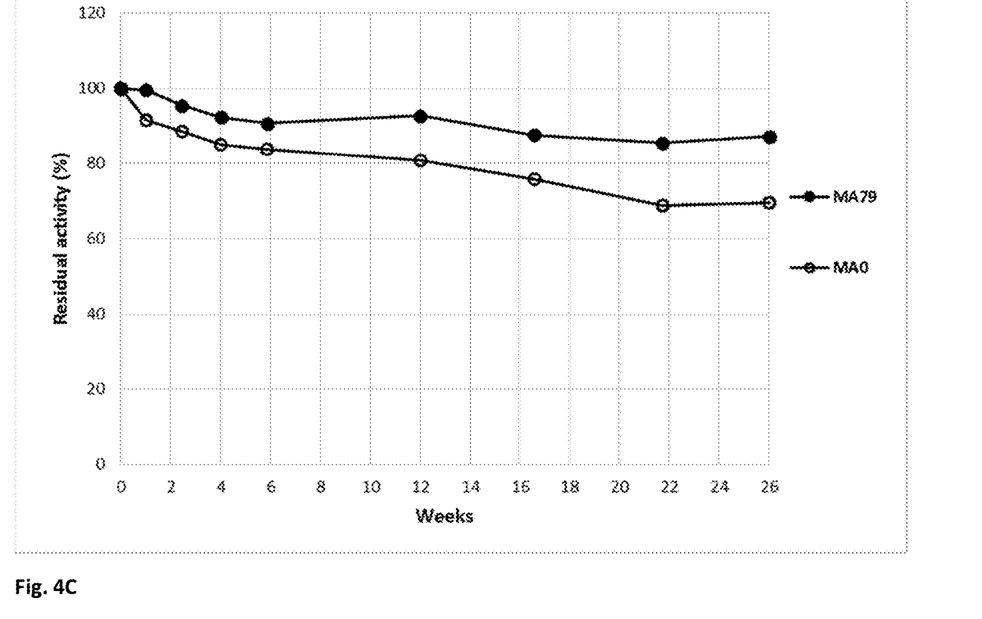
FIG. 4C shows the stability of variant MA79 compared to parental cellulase MA0 as residual activity in commercial liquid detergent at room temperature (approx. 20-22° C.) in the presence of protease.

Results of tests obtained in commercial liquid detergent with protease are shown in FIGS. 4A-C. The long term stability of variant MA79 was considerably improved compared to MA0 at all temperatures, especially at 37° C.

Figure 5:
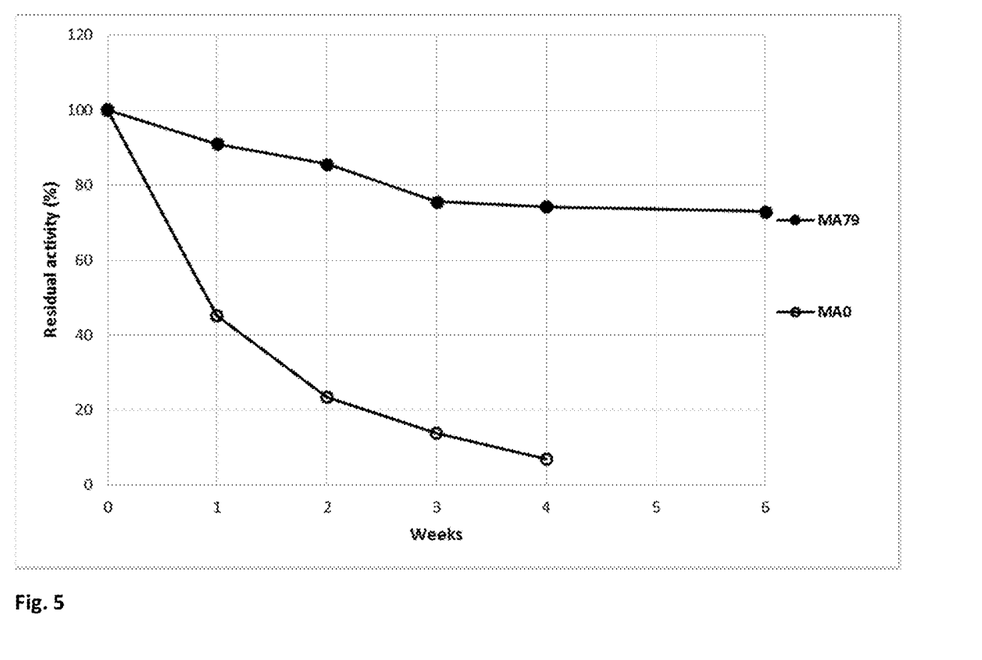
FIG. 5 shows the stability of variant MA79 compared to parental cellulase MA0 as residual activity in commercial protease containing I&I detergent at 37° C.

Stability tests with variant MA79 and MA0 were carried out also in a commercial MI (Industrial & Institutional) detergent formulation containing protease and other enzymes except cellulase. A 0.5% w/w amount of cellulase preparation was added to the detergent and samples were incubated at 37° C. for 6 weeks. Variant MA79 showed remarkably better stability than MA0 also in this I&I detergent (FIG. 5).

Example 5

Long Term Stability of Variant MA79 in Liquid Detergent Measured as Antigreying Performance The stability of variant MA79 compared to the parental MA0 cellulase was evaluated also as antigreying performance. Antigreying tests similar to that described in Example 3 were carried out with detergent samples stored for 88 and 193 days at 30° C. Cellulases were initially added to the detergent in such amount that dosage would be 0.2 activity units (NCU) per liter of wash solution. Performance of stored samples was compared to washes, in which the enzymes had been added fresh into the washing liquor containing detergent and carbon black and results were calculated as relative performance indicating the residual performance level.

Figure 6:
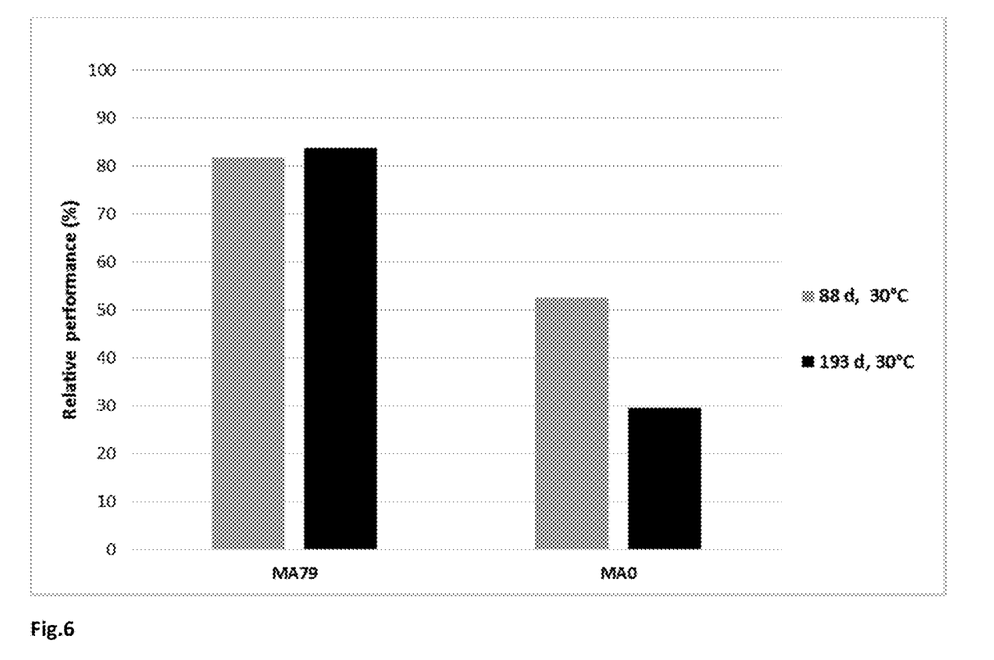
FIG. 6 shows the relative antigreying performance of variant MA79 compared to parental cellulase MA0 after 88 d and 193 d storage in commercial liquid detergent in the presence of protease at 30° C.

Results in FIG. 6 show that variant MA79 had still excellent antigreying performance after storage of over 6 months at elevated temperature like 30° C. The performance of MA0 was considerably reduced compared to MA79 already after 12 weeks.

Example 6

Stability of Variant MA79 in Liquid Detergents Compared to Commercial Cellulases A production like sample was prepared from pilot scale fermentation sample of MA79 and retested for stability in liquid detergents at various temperatures for 6 weeks, using preparation of parental cellulase MA0 and/or commercial cellulase Celluclean 5000L (Novozymes, Denmark) for comparison.

Tests were carried out in commercial liquid detergent (described in Table 2/Example 2) in the presence of added protease like described in Example 4. Also a concentrated liquid detergent containing protease and other enzymes except cellulase was tested. Cellulases at 0.5% w/w were added to the detergents.

Figure 7:
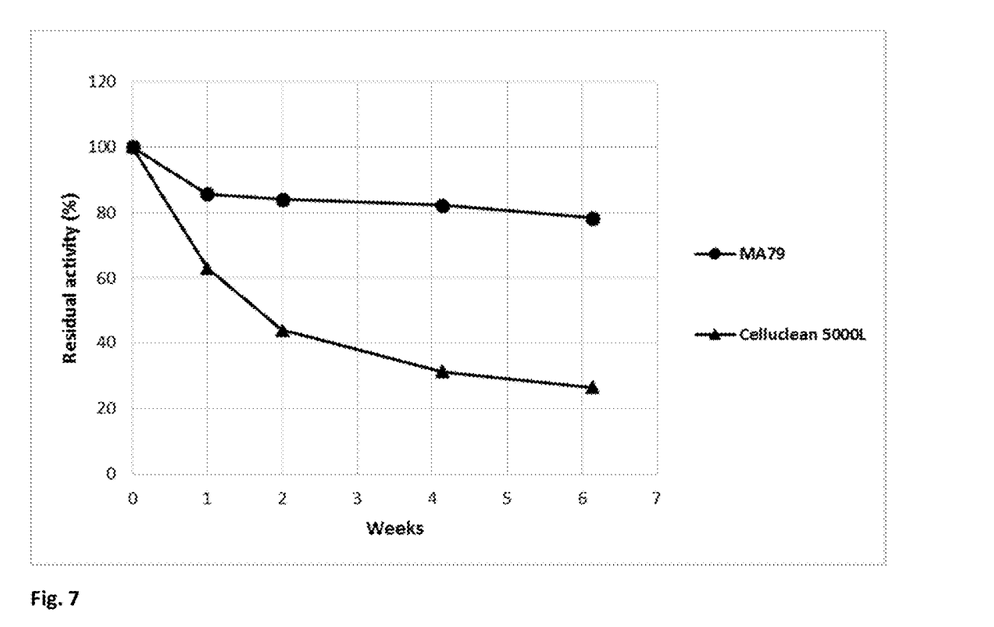
FIG. 7 shows the stability of variant MA79 compared to commercial cellulase Celluclean 5000L (Novozymes) as residual activity in commercial liquid detergent at 37° C. in the presence of protease.
Figure 8A:
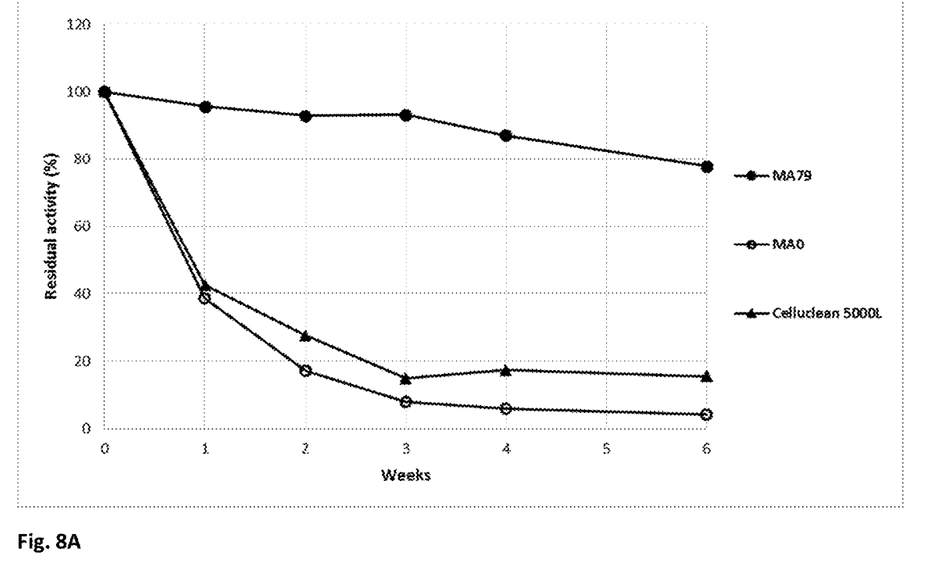
FIG. 8A shows the stability of variant MA79 compared to parental cellulase MA0 and commercial cellulase Celluclean 5000L (Novozymes) as residual activity in protease containing liquid detergent concentrate at 37° C.
Figure 8B:
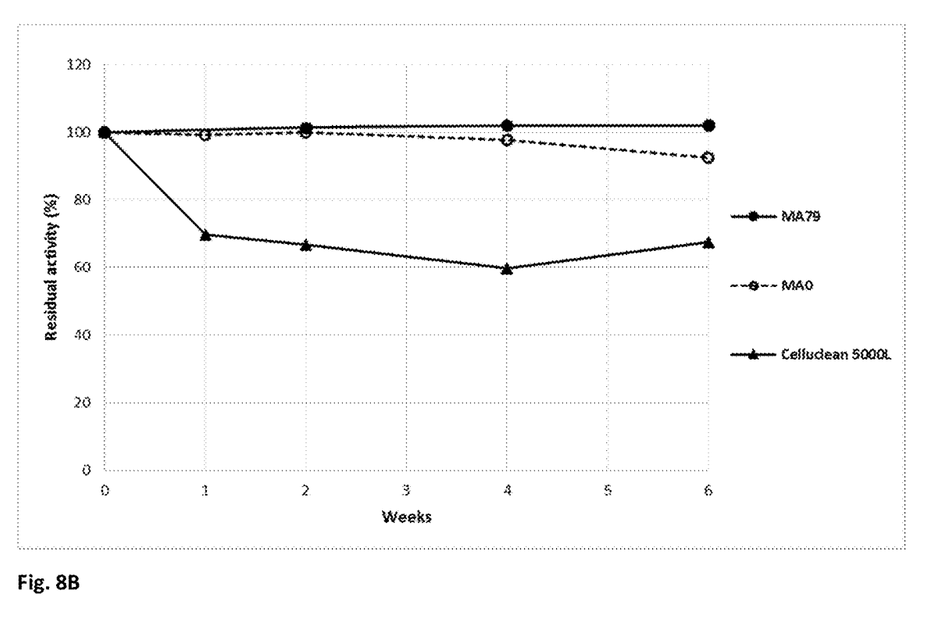
FIG. 8B shows the stability of variant MA79 compared to parental cellulase MA0 and commercial cellulase Celluclean 5000L (Novozymes) as residual activity in protease containing liquid detergent concentrate at 30° C.

Based on results shown in FIG. 7 variant MA79 had considerably better stability compared to Celluclean 5000L in commercial liquid detergent at 37° C. Results obtained with another detergent, liquid detergent concentrate show that variant MA79 had significantly better stability than both MA0 and Celluclean 5000L at 37° C. (FIG. 8A). In this detergent the stability of MA79 was better than Celluclean 5000L also at 30° C. (FIG. 8B) and at room temperature approx. 20-22° C. (data not shown).

Example 7

Screening of MA0 Variants MA80-MA116 Based on Stability in Commercial Liquid Detergent MA0 variants MA80-MA116 produced in *Trichoderma* as described in Example 1 are tested as described in Examples 2 and 4. Parental cellulase MA0 is used as reference. Several variants show improved stability in commercial liquid detergent compared to the parental MA0 cellulase. In addition several variants show improved long-term stability in commercial detergents.

REFERENCES

Bailey M and Nevalainen H. 1981. Induction, isolation and testing of stable *Trichoderma reesei* mutants with improved production of solubilizing cellulase. Enzyme Microb. Technol. 3:153-157.

Haakana H, Miettinen-Oinonen A, Joutsjoki V, Mäntylä A, Suominen P and Vehmaanperä J. 2004. Cloning of cellulase genes from *Melanocarpus albomyces* and their efficient expression in *Trichoderma reesei*. Enzyme Microb. Technol. 34:159-167.

Henrissat B. 1991. A classification of glycosyl hydrolases based on amino acid sequence similarities. Biochem. J. 280:309-316.

Henrissat B and Bairoch A. 1993. New families in the classification of glycosyl hydrolases based on amino acid sequence similarities. Biochem. J. 293:781-788.

Henrissat B and Bairoch A. 1996. Updating the sequence-based classification of glycosyl hydrolases. Biochem. J. 316:695-696.

Joutsjoki V V, T K Torkkeli and K M H Nevalainen. 1993. Transformation of *Trichoderma reesei* with the Hormoconis resinae glucoamylase P (gamP) gene: production of a heterologous glucoamylase by *Trichoderma reesei*. Curr. Genet. 24:223-228.

Karhunen T, A Mäntylä, K M H Nevalainen and P L Suominen. 1993. High frequency one-step gene replacement in *Trichoderma reesei*. I. Endoglucanase I overproduction. Mol. Gen. Genet. 241:515-522.

Paloheimo M, A Mäntylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rättö, E Salminen and J Knowles. 1987. A versatile transformation system for the cellulolytic filamentous fungus *Trichoderma reesei*. Gene 61:155-164.

Sambrook J and D W Russell. 2001. Molecular cloning, a laboratory manual. Cold Spring Harbor Laboratory, New York, US.

---

The invention claimed is:

1. A cellulase variant polypeptide, or an active fragment thereof, wherein the cellulase variant polypeptide or active fragment thereof has cellulase activity and comprises an amino acid sequence having at least 90% identity to residues 22-235 of SEQ ID NO:1 comprising a substitution at one or more amino acid position(s) selected from 22 and 122, wherein at position 22 G is substituted to A, S or V and at position 122 N is substituted to A, S, G, T, V, L or I, wherein the amino acid positions of said variant polypeptide or active fragment thereof are numbered by correspondence with the mature amino acid sequence of SEQ ID NO:3.

2. The cellulase variant polypeptide or active fragment thereof of claim 1, further comprising a substitution or deletion at one or more amino acid positions comprising 2, 33, 35, 39, 44, 48, 54, 75, 82, 92, 99, 108, 174, 175, 177, 194, 205, 206, 207, 208, 209, 210, 211, 212, 213 or 214.

3. The cellulase variant polypeptide or active fragment thereof of claim 1, wherein the cellulase variant polypeptide or active fragment thereof further comprises one or more of the following substitutions or deletions:

N2W, N2R, A33R, F35W, F35M, H39P, H39S, V44R, V44Q, V44W, V44L, E48D, S54M, S54A, S54T, S54L, S54V A75H, A75S, A75R, E82S, E82R, E82W, T92I, A99Q, T108I, Q174R, N175D, D177Q, D177E, A194Q, G205T, F206H, A207R, A207S, del(A207-A214), del(V208-A214), del(F209-A214), del(K210-A214), del(A211-A214), del(P212-A214) or del(S213-A214).

4. The cellulase variant polypeptide or active fragment thereof of claim 1, wherein the cellulase variant polypeptide or active fragment thereof comprises at least one further substitution or deletion.

5. The cellulase variant polypeptide or active fragment thereof of claim 1, wherein the cellulase variant polypeptide or active fragment thereof comprises at least one further substitution selected from the substitutions at positions 2, 35, 44, 54, 75, 82, 108, 174, 177, 205, 206 or 207.

6. The cellulase variant polypeptide or active fragment thereof of claim 1, wherein the cellulase variant polypeptide or active fragment thereof comprises at least one further deletion selected from the following: del(A207-A214), del(V208-A214), del(F209-A214), del(K210-A214), del(A211-A214), del(P212-A214) or del(S213-A214).

7. An enzyme composition comprising the cellulase variant polypeptide according to claim 1.

8. The enzyme composition according to claim 7 wherein said composition further comprises other enzymes selected from the group consisting of protease, amylases, cellulases, lipases, xylanases, mannanases, cutinases, esterases, phytases, DNAses, pectinases, pectate lyases, pectinolytic enzymes, carbohydrases, arabinases, galactanases, xanthanases, xyloglucanases, laccases, peroxidases and oxidases with or without a mediator.

9. The enzyme composition according to claim 7, wherein said composition comprises a suitable additive selected from the group consisting of a stabilizer, a buffer, a surfactant, a builder, a bleaching agent, a mediator, an anti-corrosion agent, an antiredeposition agent, a caustic, an abrasive, an optical brightener, a dye, a pigment, and a preservative.

10. The enzyme composition according to claim 7, wherein said enzyme composition is in the form of a solution, dispersion, paste, powder, granule, granulate, coated granulate, tablet, cake, crystal, crystal slurry, gel, or pellet.

11. The cellulase variant polypeptide or active fragment thereof according to claim 1 for use in detergents, in treating fiber, in wood-derived pulp, in biomass hydrolysis, in food or feed application, or in any application involving modification, degradation or removal of cellulose containing material.

12. A method for antigreying, stain removal, fiber and color care, biostoning or biofinishing comprising adding the cellulase variant polypeptide according to claim 1 to liquid used in treating cotton containing fabric or garments or other textile materials.

13. The method of claim 12, wherein the textile materials are manufactured of natural cellulose containing fibers or manmade cellulose containing fibers or are mixtures thereof.

14. A detergent composition comprising the cellulase variant polypeptide or active fragment thereof according to claim 1.

15. The detergent composition of claim 14 in the form of liquid detergent or a solid detergent.

16. The detergent composition according to claim 14 comprising one or more enzymes selected from the group consisting of proteases, amylases, cellulases, lipases, xylanases, mannanases, cutinases, esterases, DNAses, pectinases, pectate lyases, pectinolytic enzymes, carbohydrases, arabinases, galactanases, xanthanases, xyloglucanases, laccases, peroxidases and oxidases, preferably from the group of proteases, amylases, cellulases and lipases.

17. A method of treating cellulosic fiber containing textile material, wherein said method comprises contacting said textile material with the detergent composition according to claim 14.

* * * * *

SEQUENCE LISTING

<160> NUMBER OF SEQ ID NOS: 3

<210> SEQ ID NO 1
<211> LENGTH: 235
<212> TYPE: PRT
<213> ORGANISM: Melanocarpus albomyces

<400> SEQUENCE: 1

```
Met Arg Ser Thr Pro Val Leu Arg Ala Leu Leu Ala Ala Ala Leu Pro
1               5                   10                  15

Leu Gly Ala Leu Ala Ala Asn Gly Gln Ser Thr Arg Tyr Trp Asp Cys
                20                  25                  30

Cys Lys Pro Ser Cys Gly Trp Ala Gly Lys Gly Pro Val Asn Gln Pro
            35                  40                  45

Val Tyr Ser Cys Asp Ala Asn Phe Gln Arg Ile His Asp Phe Asp Ala
    50                  55                  60

Val Ser Gly Cys Glu Gly Gly Pro Ala Phe Ser Cys Ala Asp His Ser
65                  70                  75                  80

Pro Trp Ala Ile Asn Asp Asn Leu Ser Tyr Gly Phe Ala Ala Thr Ala
                85                  90                  95

Leu Ser Gly Gln Thr Glu Glu Ser Trp Cys Cys Ala Cys Tyr Ala Leu
                100                 105                 110

Thr Phe Thr Ser Gly Pro Val Ala Gly Lys Thr Met Val Val Gln Ser
            115                 120                 125

Thr Ser Thr Gly Gly Asp Leu Gly Ser Asn His Phe Asp Leu Asn Ile
        130                 135                 140

Pro Gly Gly Gly Val Gly Leu Phe Asp Gly Cys Thr Pro Gln Phe Gly
145                 150                 155                 160

Gly Leu Pro Gly Ala Arg Tyr Gly Gly Ile Ser Ser Arg Gln Glu Cys
                165                 170                 175

Asp Ser Phe Pro Glu Pro Leu Lys Pro Gly Cys Gln Trp Arg Phe Asp
            180                 185                 190

Trp Phe Gln Asn Ala Asp Asn Pro Ser Phe Thr Phe Glu Arg Val Gln
        195                 200                 205

Cys Pro Glu Glu Leu Val Ala Arg Thr Gly Cys Arg Arg His Asp Asp
    210                 215                 220

Gly Gly Phe Ala Val Phe Lys Ala Pro Ser Ala
225                 230                 235
```

<210> SEQ ID NO 2
<211> LENGTH: 849
<212> TYPE: DNA

<213> ORGANISM: Melanocarpus albomyces

<400> SEQUENCE: 2

```
atgcgctcta ctcccgttct ccgcgccctc ctggccgcag cattgcccct cggggccctc      60
gccgccaacg gtcagtccac gaggtaactg atcacccgcc tcattacgcg tgccgaccgg     120
accgcgttca gggctcactg ctcaccgcat ccagatactg ggactgctgc aagccgtcgt     180
gcggctgggc cggaaagggc cccgtgaacc agcccgtcta ctcgtgcgac gccaacttcc     240
agcgcatcca cgacttcgat gccgtctcgg gctgcgaggg cggccccgcc ttctcgtgcg     300
ccgaccacag ccctgggcc attaatgaca acctctcgta cggcttcgcg gcgactgcac     360
tcagcggcca gaccgaggag tcgtggtgct gtgcctgcta cgcgtgagtg tgcttgggcc     420
caacgtcggt gattccggag ttcagaccac tgacccagcg accgctcgc cagtctgacc      480
tttacatcgg gtcccgtggc cggcaagacc atggtcgtcc agtcgaccag cacgggcggc     540
gacctcggca gcaaccactt cgacctcaac atccccggcg gcggcgtcgg cctcttcgac     600
ggctgcactc cccagttcgg cggcctcccg ggcgcacggt acggcggcat ctcgtcgcgc     660
caggagtgcg actcgttccc cgagccgctc aagcccggct gccagtggcg cttcgactgg     720
ttccagaacg ccgacaaccc gtcctttacc ttcgagcggg tccagtgccc cgaggagctg     780
gtcgctcgga ccggctgcag gcgccacgac gacggcggct tcgccgtctt caaggccccc     840
agcgcctga                                                             849
```

<210> SEQ ID NO 3
<211> LENGTH: 214
<212> TYPE: PRT
<213> ORGANISM: Melanocarpus albomyces

<400> SEQUENCE: 3

```
Ala Asn Gly Gln Ser Thr Arg Tyr Trp Asp Cys Cys Lys Pro Ser Cys
  1               5                  10                  15

Gly Trp Ala Gly Lys Gly Pro Val Asn Gln Pro Val Tyr Ser Cys Asp
             20                  25                  30

Ala Asn Phe Gln Arg Ile His Asp Phe Asp Ala Val Ser Gly Cys Glu
         35                  40                  45

Gly Gly Pro Ala Phe Ser Cys Ala Asp His Ser Pro Trp Ala Ile Asn
     50                  55                  60

Asp Asn Leu Ser Tyr Gly Phe Ala Ala Thr Ala Leu Ser Gly Gln Thr
 65                  70                  75                  80

Glu Glu Ser Trp Cys Cys Ala Cys Tyr Ala Leu Thr Phe Thr Ser Gly
                 85                  90                  95

Pro Val Ala Gly Lys Thr Met Val Val Gln Ser Thr Ser Thr Gly Gly
            100                 105                 110

Asp Leu Gly Ser Asn His Phe Asp Leu Asn Ile Pro Gly Gly Gly Val
        115                 120                 125

Gly Leu Phe Asp Gly Cys Thr Pro Gln Phe Gly Gly Leu Pro Gly Ala
    130                 135                 140

Arg Tyr Gly Gly Ile Ser Ser Arg Gln Glu Cys Asp Ser Phe Pro Glu
145                 150                 155                 160

Pro Leu Lys Pro Gly Cys Gln Trp Arg Phe Asp Trp Phe Gln Asn Ala
                165                 170                 175
```

```
Asp Asn Pro Ser Phe Thr Phe Glu Arg Val Gln Cys Pro Glu Glu Leu
            180             185             190

Val Ala Arg Thr Gly Cys Arg His Asp Asp Gly Gly Phe Ala Val
        195             200             205

Phe Lys Ala Pro Ser Ala
    210
```